(12) United States Patent
Newton et al.

(10) Patent No.: US 9,036,149 B2
(45) Date of Patent: *May 19, 2015

(54) ELECTROCHEMICAL SENSOR WITH DIAMOND ELECTRODES

(75) Inventors: Mark Edward Newton, Warwickshire (GB); Julie Victoria MacPherson,
(Continued)

(73) Assignee: Element Six Technologies Limited (GB)

( * ) Notice: Subject to any disclaimer, the term of this patent is extended or adjusted under 35 U.S.C. 154(b) by 8 days.
This patent is subject to a terminal disclaimer.

(21) Appl. No.: 14/115,067
(22) PCT Filed: May 2, 2012
(86) PCT No.: PCT/EP2012/058038
§ 371 (c)(1), (2), (4) Date: Oct. 31, 2013
(87) PCT Pub. No.: WO2012/156203
PCT Pub. Date: Nov. 22, 2012

(65) Prior Publication Data
US 2014/0069811 A1 Mar. 13, 2014

Related U.S. Application Data

(60) Provisional application No. 61/487,514, filed on May 18, 2011.

(30) Foreign Application Priority Data

May 18, 2011 (GB) .................................. 1108339.1

(51) Int. Cl.
*G01N 21/75* (2006.01)
(Continued)

(52) U.S. Cl.
CPC ............ *G01N 27/4163* (2013.01); *G01N 21/75* (2013.01); *G01N 27/48* (2013.01); *G01N 27/308* (2013.01)

(58) Field of Classification Search
CPC ... G01N 27/416; G01N 27/48; G01N 27/308; G01N 21/75; G01N 21/12; G01N 23/223
USPC ........... 378/44, 45; 356/326, 432; 250/361 R, 250/370.09; 205/81; 204/406
See application file for complete search history.

(56) References Cited

U.S. PATENT DOCUMENTS 7,883,617 B2  2/2011  Einaga et al.
2003/0170906 A1  9/2003  Swain et al.
2011/0308942 A1*  12/2011  Liu et al. .................... 204/400

FOREIGN PATENT DOCUMENTS

CH        678662 A5    10/1991
(Continued)

OTHER PUBLICATIONS

Wang et al. (Analytical Chemistry, 2007, vol. 79, No. 12, pp. 4427-4432).*

(Continued)

*Primary Examiner* — Jennifer Dieterle
(74) *Attorney, Agent, or Firm* — Bryan Cave LLP

(57) ABSTRACT

An electrochemical sensor comprising: a reference electrode (4) formed of an electrically conductive synthetic doped diamond material and configured to be located in electrical contact with a solution (8) to be analysed; a sensing electrode (2) formed of an electrically conductive synthetic doped diamond material and configured to be located in contact with the solution (8) to be analysed; an electrical controller (10) configured to conduct stripping voltammetric measurements by applying a voltage to the sensing electrode (2), to change the applied voltage relative to the reference electrode (4), and to measure an electric current flowing through the sensing electrode (2) thereby generating voltammetry data; and a calibration system configured to provide an in-situ calibration for providing a reference point in the voltammetric data since the potential of the diamond reference electrode is non fixed and floating. Consequently, assigning of peaks (M1, M2, M3) in the voltammetry data to chemical species (M1, M2, M3) is possible, thereby allowing the type and concentration of chemical species in the solution (8) to be determined. The in-situ calibration consists of: 1-using a spectrometer for X-rays, Gamma rays or fluorescence measurements integrated in the sensor, 2-using a known redox couple added to the solution that will provide a reference peak in the voltammetric data, or 3-producing in-situ ionic species at the vicinity of the reference electrode.

17 Claims, 10 Drawing Sheets

(72) Inventors: Warwickshire (GB); Laura Anne Hutton, Warwickshire (GB); Timothy Peter Mollart, Oxfordshire (GB); Geoffrey Alan Scarsbrook, Oxfordshire (GB)

(51) Int. Cl.
*G01N 27/416* (2006.01)
*G01N 27/48* (2006.01)
*G01N 27/30* (2006.01)

(56) References Cited

FOREIGN PATENT DOCUMENTS

| | | | |
|---|---|---|---|
| EP | 1514090 | B1 | 3/2005 |
| EP | 1891423 | B1 | 2/2012 |
| EP | 1514090 | B1 | 11/2013 |
| GB | 2476237 | A | 6/2011 |
| JP | 2001091499 | A | 4/2001 |
| JP | 2005257320 | A | 9/2005 |
| JP | 2007040796 | A | 2/2007 |
| JP | 2010271236 | A | 12/2010 |
| JP | 2012127943 | A | 7/2012 |
| WO | 97/15820 | A1 | 5/1997 |
| WO | 03/085173 | A2 | 10/2003 |
| WO | 03/104765 | A2 | 12/2003 |
| WO | 2005/012894 | A1 | 2/2005 |
| WO | 2007/107844 | A1 | 9/2007 |
| WO | 2008/015435 | A1 | 2/2008 |
| WO | 2008/108124 | A1 | 9/2008 |

OTHER PUBLICATIONS

Hutton et al. (Journal Physical Chem, 2010, pp. 1649-1658).*
Stotter et al (Analytical Chemistry, 2002, vol. 74, No. 23, pp. 5924-5930).*
Griesel et al. (Spectrochimica Acta B, Atomic Spectroscopy, 2001, vol. 56, No. 11, pp. 2107-2115).*
International Search Report for PCT/EP2012/058761 dated Jul. 3, 2012.
International Search Report for PCT/EP2012/058038 dated Jun. 25, 2012.
Varney et al: "All-diamond micro-electrode arrays for neural recordings and diamond electrochemistry," Nano/Micro Engineered and Molecular Systems (NEMS), 2010 5th IEEE International Conference on IEEE, Piscataway, NJ, USA, Jan. 20, 2010, pp. 1116-1119.
Hutton et al: "Factors Controlling Stripping Voltammetry of Lead at Polycrystalline 80ron Doped Diamond Electrodes: New Insights from High-Resolution Microscopy," Analytical Chemistry, vol. 83, No. 3, Feb. 1, 2011, pp. 735-745.
Johnson et al., "In situ calibrated oxygen electrode," Sensors and Actuators B: Chemical, vol. 105, No. 2, 2005, 322-328.
McGAW et al., "A comparison of boron-doped diamond thin-film and Hg-coated glassy carbon electrodes for anodic stripping voltammetric determination of heavy metal ions in aqueous media," Analytica Chimica Acta, vol. 575, 2006, pp. 180-189.
Dai et al., "Measurements: Optically Transparent Carbon Electrodes," Analytical Chemistry, 15-22, Jan. 1, 2008.
Dai et al., "Optically Transparent Diamond Electrode for Use in IR Transmission Spectroelectrochemical Measurements," Analytical Chemistry, vol. 79, No. 19, Oct. 1, 2007.
Haymond et al., "Spectroelectrochemical responsiveness of a free-standing, boron-doped diamond, optically transparent electrode towards ferrocene," Analytica Chimica Acta, 500, 137-144 (2003).
Stotter et al., "Optical and Electrochemical properties of Optically Transparent, Boron-Doped Diamond Thin Films Deposited on Quartz," Analytical Chemistry, vol. 74, No. 23, Dec. 1, 2002.
Zhang et al., "A novel boron-doped diamond (BDD)-coated platinum mesh electrode for spectroelectrochemistry," Journal of Electroanalytical Chemistry 603, 135-141 (2007).
Ward Jones et al., "Stripping Analysis using Boron-Doped Diamond Electrodes," Current Analytical Chemistry, 4, 170-176 (2008).
Alov et al., "Formation of binary and ternary metal deposits on glass-ceramic carbon electrode surfaces: electron-probe X-ray microanalysis, total-reflection X-ray fluorescence analysis, X-ray photoelectron spectroscopy and scanning electron microscopy study," Spectrochimica Acta Part B, 58, 735-740 (2003).
Peeters et al., "Quantitative synchrotron micro-XRF study of CoTSPc and CuTSPc thin-films deposited on gold by cyclic voltammetry," Journal of Analytical Atomic Spectrometry, 22, 493-501 (2007).
Ritschel et al., "An electrochemical enrichment procedure for the determination of heavy metals by total-reflection X-ray fluorescence spectroscopy," Spectrochimica Acta Part B, 54, 1449-1454 (1999).
Alov et al., "Total-reflection X-ray fluorescence study of electro-chemical deposition of metals on a glass-ceramic carbon electrode surface," Spectrochimica Acta Part B, 56, 2117-2126 (2001).
Hutton, "Electrodeposition of Nickel Hydroxide Nanoparticles on Boron-Doped Diamond Electrodes for Oxidative Electrocatalysis," J. Phys. Chem. C, 2011, 115, 1649-1658.
Wang et al., "Detection of Heavy Metal Ions in Water by High Resolution Surface Plasmon Resonance Spectroscopy Combined with Anodic Stripping Voltammetry," Analytical Chemistry, 2007, vol. 79, No. 12, 4427-4432.
Griesel et al., "Electro-Deposition as a Sample Preparation Technique for Total Reflection X-Ray Fluorescence Analysis," Spectrochimica Acta B, Atomic Spectroscopy, 2001, vol. 56, No. 11, 2107-2115.
Search Report for GB1208271.5 dated Aug. 30, 2012.
Search Report for GB1108342.5 dated Sep. 6, 2011.
GB Search Report for GB1207688.1 dated Aug. 15, 2012.

* cited by examiner

Fig 3
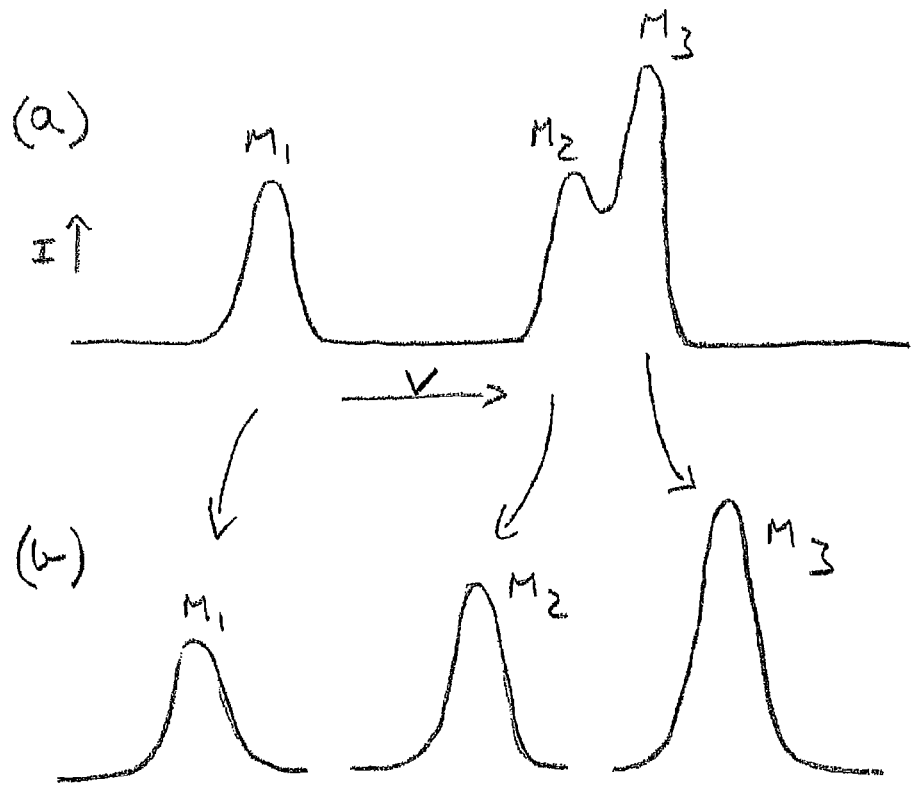
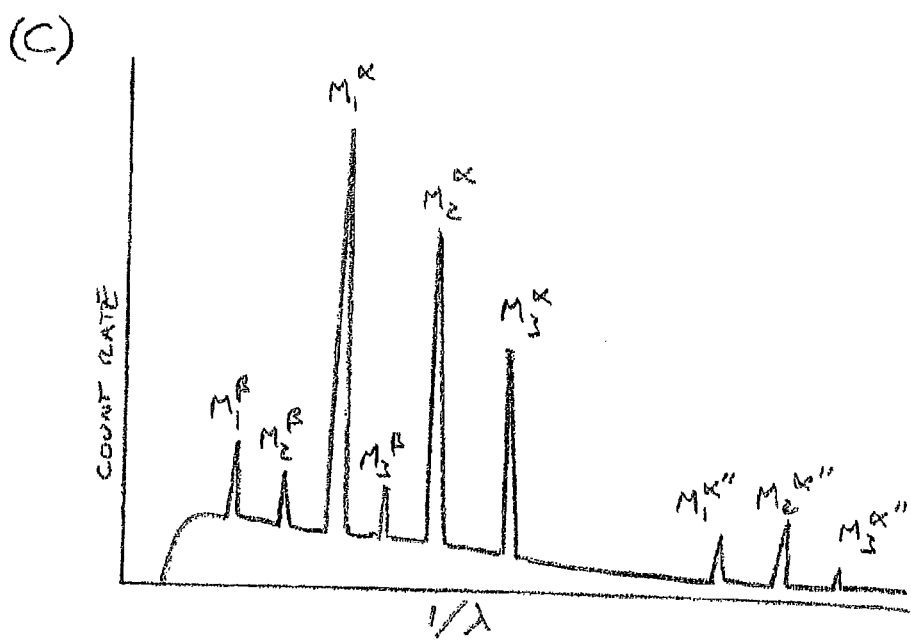

Fig. 6

Identify the peak in the voltammetry data associated with a known redox couple in the solution, the known redox couple having a known potential versus a standard reference potential.

Measure a shift in the peak of the known redox couple relative to its known potential versus the standard reference potential.

Use the measured shift to calibrate the voltammetry data relative to the standard reference potential.

Use the calibrated voltammetry data to assign peaks to chemical species which have a known potential relative to the standard reference potential.

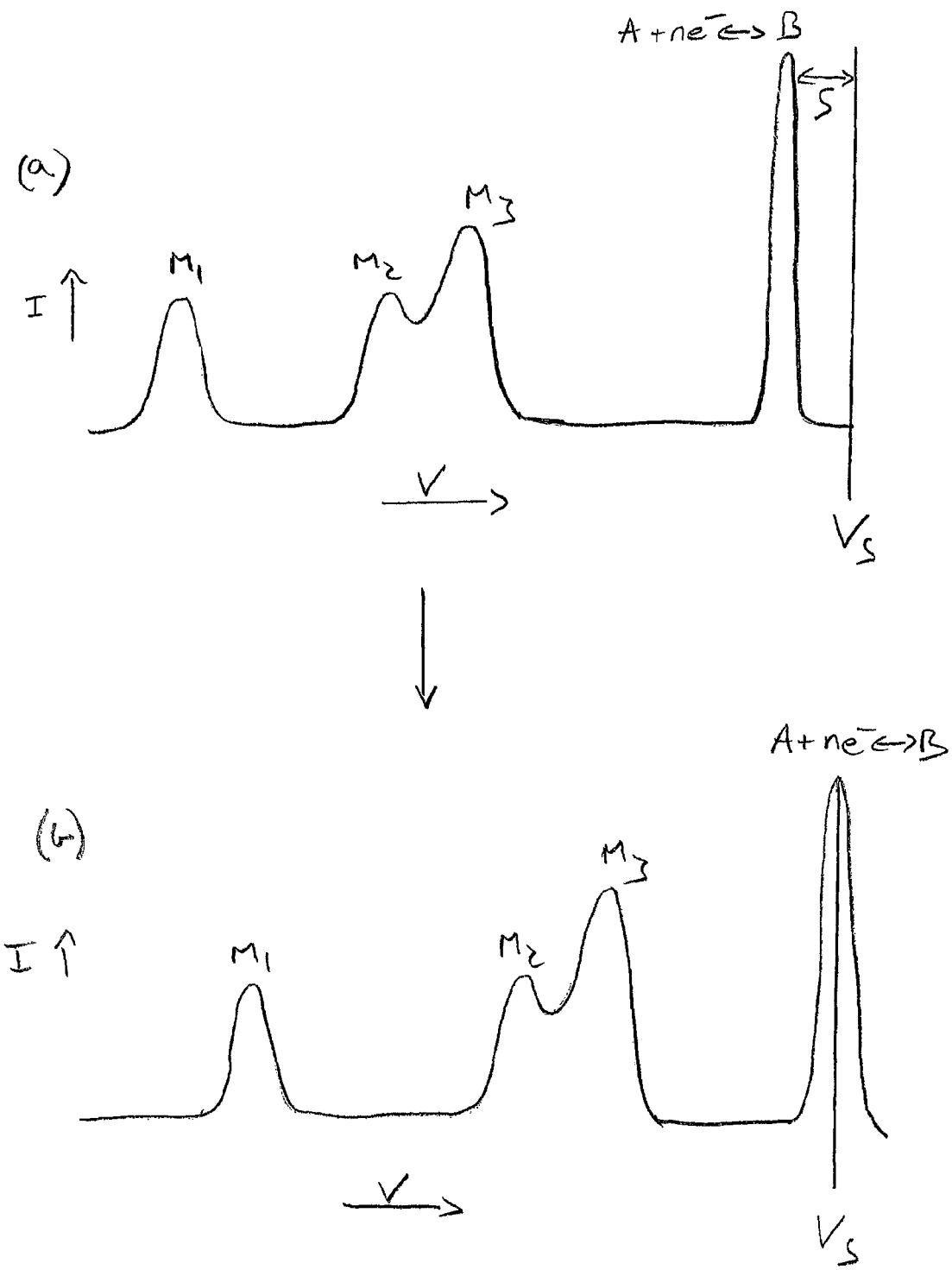

Fig. 8

| Produce a constant and known concentration of potential determining ions in-situ over the reference electrode, the reference electrode having a known potential in a solution comprising said concentration of potential determining ions |

↓

| Use the known potential to calibrate the voltammetry data. |

↓

| Use the calibrated voltammetry data to assign peaks to chemical species based on their known potential. |

ELECTROCHEMICAL SENSOR WITH DIAMOND ELECTRODES

FIELD OF INVENTION

Certain embodiments of the present invention relate to electrochemical sensors and the use of such sensors for chemical species detection in solution. Particular embodiments relate to the use of synthetic diamond material for forming electrodes in such applications.

BACKGROUND OF INVENTION

Electrochemical sensors are well known. It has also been proposed in the prior art to provide a diamond based electrochemical sensor. Diamond can be doped with boron to form semi-conductive or fully metallic conductive material for use as an electrode. Diamond is also hard, inert, and has a very wide potential window making it a very desirable material for use as a sensing electrode for an electrochemical cell, particularly in harsh chemical, physical, and/or thermal environments which would degrade standard metal based electrochemical sensors. In addition, it is known that the surface of a boron doped diamond electrode may be functionalized to sense certain species in a solution adjacent the electrode.

One problem with using diamond in such applications is that diamond material is inherently difficult to manufacture and form into suitable geometries for sophisticated electrochemical analysis. To date, diamond electrodes utilized as sensing electrodes in an electrochemical cell have tended to be reasonably simple in construction and mostly comprise the use of a single piece of boron doped diamond configured to sense one physical parameter or chemical species at any one time. More complex arrangements have involved introducing one or more channels into a piece of boron doped diamond through which a solution can flow for performing electrochemical analysis. However, due to the inherent difficulties involved in manufacturing and forming diamond into multi-structural components, even apparently relatively simple target structures can represent a significant technical challenge.

In terms of prior art arrangements, WO 2005012894 describes a microelectrode comprising a diamond layer formed from electrically non-conducting diamond and containing one or more pin-like projections of electrically conducting diamond extending at least partially through the layer of non-conducting diamond and presenting areas of electrically conducting diamond at a front sensing surface. In contrast, WO2007107844 describes a microelectrode array comprising a body of diamond material including alternating layers of electrically conducting and electrically non-conducting diamond material and passages extending through the body of diamond material. In use, fluid flows through the passages and the electrically conducting layers present ring-shaped electrode surfaces within the passages in the body of diamond material.

More recently, it has been proposed that high aspect ratio boron doped diamond electrodes have improved sensing capability when compared with other boron doped diamond electrode arrangements. That is, it has been found to be highly advantageous to provide boron doped diamond electrodes which have a high length/width ratio at a sensing surface. Furthermore, it has been found that an array of high aspect ratio boron doped diamond electrodes providing a band sensor structure can be utilized to provide multiple sensing functions.

The previously described arrangements may comprise optically opaque, electrically conductive boron doped diamond electrodes spaced apart by optically transparent, non-conductive intrinsic diamond layers. The optically opaque, electrically conductive boron doped diamond electrodes can be driven to perform electrochemical measurements of species in aqueous solution. It has also been suggested that electrochemical techniques can also be combined with optical techniques such as spectroscopic measurements by using the non-conductive intrinsic diamond layers as an optical window as described in WO2007/107844. As such, electrochemical measurements can be performed at the optically opaque, electrically conductive boron doped diamond electrodes and optical measurements of the solution can be performed through non-conductive intrinsic diamond layers.

Swain et al. describe a combined electrochemistry-transmission spectroscopy technique for analysing chemical species in solution. The technique uses an electrochemical cell comprising an optically transparent carbon electrode (e.g. a thin film of boron-doped diamond on an optically transparent substrate), a thin solution layer, and an optical window mounted opposite the optically transparent carbon electrode such that transmission spectroscopy can be performed on species within the solution. The optically transparent carbon electrode is used to oxidize and reduce species in the solution. In situ IR and UV-visible spectroscopy is performed through the optically transparent carbon electrode to analyse dissolved species in the solution. Dissolved species which have different IR and UV-visible spectra in different oxidation states can be analysed. Although boron-doped diamond material is opaque at high boron concentrations, thin films of such material have a reasonable optical transparency. It is described that the ability to cross-correlate electrochemical and optical data may provide new insights into the mechanistic aspects of a wide variety of electrochemical phenomena including structure-function relationships of redox-active proteins and enzymes, studies of molecular absorption processes, and as a dual signal transduction method for chemical and biological sensing [see "Measurements: Optically Transparent Carbon Electrodes" Analytical Chemistry, 15-22, 1 Jan. 2008, "Optically Transparent Diamond Electrode for Use in IR Transmission Spectroelectrochemical Measurements" Analytical Chemistry, vol. 79, no. 19, Oct. 1, 2007, "Spectroelectrochemical responsiveness of a freestanding, boron-doped diamond, optically transparent electrode towards ferrocene" Analytica Chimica Acta 500, 137-144 (2003), and "Optical and Electrochemical Properties of Optically Transparent, Boron-Doped Diamond Thin Films Deposited on Quartz" Analytical Chemistry, vol. 74, no. 23, 1 Dec. 2002]. Zhang et al. have also reported the use of an optically transparent boron-doped diamond thin film electrode for performing combined electrochemistry-transmission spectroscopy analysis [see "A novel boron-doped diamond-ciated platinum mesh electrode for spectroelectrochemistry" Journal of Electroanalytical Chemistry 603. 135-141 (2007)].

As an alternative to analysing chemical species while in solution as described above, one useful electro-chemical analysis technique involves applying a suitable voltage to a sensing electrode to electro-deposit chemical species out of solution onto the sensing electrode and then change the voltage to strip the species from the electrode. Different species strip from the electrode at different voltages. Measurement of electric current during stripping generates a series of peaks associated with different species stripping from the sensing electrode at different voltages. Such a stripping voltammetry technique can be used to analyse heavy metal content.

The use of a boron-doped diamond sensor in a stripping voltammetry technique has been described in U.S. Pat. No.

7,883,617B2 (University of Keio). Jones and Compton also describe the use of a boron-doped diamond sensor in stripping voltammetry techniques [see "Stripping Analysis using Boron-Doped Diamond Electrodes" Current Analytical Chemistry, 4, 170-176 (2008)]. This paper includes a review which covers work on a wide range of analytical applications including trace toxic metal measurement and enhancement techniques for stripping voltammetry at boron-doped diamond electrodes including the use of power ultrasound, microwave radiation, lasers and microelectrode arrays. In the described applications a boron-doped diamond material is used for the working/sensing electrode in combination with standard counter and reference electrodes.

McGraw and Swain also describe using stripping voltammetry to analysis metal ions in solution using an electrochemical cell comprising a boron-doped diamond working electrode in combination with standard counter and reference electrodes (a carbon rod counter electrode and a silver/silver chloride reference electrode). It is concluded that boron-doped diamond is a viable alternative to Hg for the anodic stripping voltammetry determination of common metal ion contaminants [see "A comparison of boron-doped diamond thin-film and Hg-coated glassy carbon electrodes for anodic stripping voltammetric determination of heavy metal ions in aqueous media" Analytica Chimica Acta 575, 180-189 (2006)].

In addition to the stripping voltammetry techniques described above, it is also known to use spectroscopic techniques for analysing electro-deposited films. For example, Peeters et al describe the use of cyclic voltammetry to electrochemically deposit cobalt and copper species onto a gold electrode using a three electrode cell comprising a saturated calomel reference electrode, a carbon counter electrode, and a gold working electrode. The gold electrodes comprising electrochemically deposited cobalt and copper species were subsequently transferred to a synchrotron radiation X-ray fluorescence (SR-XRF) facility for SR-XRF analysis to determine the heterogeneity of the deposited layers and the concentrations of Co and Cu. A comparison of SR-XRF results with electrochemical data was used to investigate the mechanism of thin film growth of the cobalt and copper containing species [see "Quantitative synchrotron micro-XRF study of CoTSPc and CuTSPc thin-films deposited on gold by cyclic voltammetry" Journal of Analytical Atomic Spectrometry, 22, 493-501 (2007)].

Ritschel et al. describe electrodeposition of heavy metal species onto a niobium cathode. The niobium cathode comprising the electrodeposited heavy metal species is then transferred to a total reflection X-ray fluorescence (TXRF) spectrometer for TXRF analysis [see "An electrochemical enrichment procedure for the determination of heavy metals by total-reflection X-ray fluorescence spectroscopy" Spectrochimica Acta Part B, 54, 1449-1454 (1999)].

Alov et al. describe electrodeposition of heavy metal species onto a glass-ceramic carbon working electrode. A standard silver chloride reference electrode and a platinum counter electrode were used in the electrochemical cell. The glass-ceramic carbon working electrode comprising the electrodeposited heavy metal species is then transferred to a total reflection X-ray fluorescence (TXRF) spectrometer for TXRF analysis [see "Total-reflection X-ray fluorescence study of electrochemical deposition of metals on a glass-ceramic carbon electrode surface" Spectrochimica Acta Part B, 56, 2117-2126 (2001) and "Formation of binary and ternary metal deposits on glass-ceramic carbon electrode surfaces: electron-probe X-ray microanalysis, total-reflection X-ray fluorescence analysis, X-ray photoelectron spectroscopy and scanning electron microscopy study" Spectrochimica Acta Part B, 58, 735-740 (2003)].

The present inventors have identified a number of potential problems with the aforementioned techniques. For example, while Swain et al. and Zhang et al. have described the use of in-situ spectroscopic techniques through a transparent electrode in an electrochemical sensor to generate spectroscopic data which is complimentary to voltammetry data, the transmission IR and UV-visible spectroscopy techniques described therein are only suitable for analysis of chemical species in solution. They are not suitable for analysing species such as heavy metals electro-deposited on an electrode. Furthermore, as the species are not concentrated by electro-deposition onto an electrode surface then low concentrations of species in solution may be below the detection limit for certain spectroscopic techniques. Further still, such spectroscopic techniques only give information about chemical species in the bulk solution and do not give information about the surface of the sensor to establish, for example, when the surface of an electrode is clean or when minerals or amalgams form on an electrode surface.

In contrast, prior art stripping voltammetry techniques on diamond electrodes are advantageous for analysing species such as heavy metals which can be electro-deposited from solution as described by Jones, Compton, McGraw and Swain. However, species discrimination in multi-metal solutions can be a problem using such techniques since the peak positions can be overlapping in stripping voltammetry data. Furthermore, the use of standard reference and counter electrodes in such arrangements means that the electrochemical sensor is not robust to harsh chemical and physical environments, even if the diamond sensing electrode is robust to such conditions.

The problem of overlapping peaks in stripping voltammetry data can potentially be solved by applying the teachings of Peeters et al., Ritschel et al., and Alov et al. These groups have suggested electro-depositing films onto gold, niobium or glass-ceramic carbon working electrodes and then extracting the electrodes from the electro-deposition apparatus and transferring the coated electrodes to a suitable device for further analysis including, for example, electron-probe X-ray microanalysis, total-reflection X-ray fluorescence analysis, X-ray photoelectron spectroscopy and scanning electron microscopy. However, this technique requires the provision of multiple devices and the extraction of coated electrode components for subsequent analysis which may not be possible for field analysis and/or in remote sensing environments, e.g. down an oil well. Furthermore, the electrodes, particularly gold, can interfere with x-ray analysis techniques such as X-ray fluorescence analysis.

Further still, the electro-deposition and electrochemical sensor apparatus described in the aforementioned documents use electrodes which are not robust to harsh chemical and physical environments. Even those documents which describe the use of synthetic boron-doped diamond material as a sensing/working electrode include less robust materials for the reference and counter electrodes. This is problematic as synthetic doped diamond material will generally be the material of choice for sensing applications in harsh chemical and/or physical environments. However, while synthetic doped diamond material has been proposed for use as a sensing/working electrode in such applications, a standard reference electrode is still required to provide a constant and fixed reference potential in order to be able to assign peaks in voltammetric data. In this regard, it should be noted that the purpose of a reference electrode is usually to maintain a constant potential with respect to the working electrode.

According to the Nernst equation the local concentration of redox active or potential determining ions will determine the reference electrode potential. Thus common reference electrodes such as the "saturated calomel electrode" and the "silver/silver chloride electrode" contain a metal coated in its sparingly soluble chloride salt in contact with a saturated concentration of chloride ions. In this way, the concentration of chloride ions next to the electrode surface is maintained at a fixed value irrespective of the solution conditions in which the electrode is placed. Commercial electrodes typically contain such an electrode housed in a glass body in contact with a solution filled with an excess of potassium chloride, separated from the main solution under test using a frit. For device fabrication this design may not be appropriate and so manufacturers often microfabricate Ag structures which they then chloridise to form a thin silver chloride coating. In solution the silver chloride dissolves to form a layer of chloride ions around the surface which can be approximated as being constant, however this is not as stable as a true reference electrode.

The issues with reference electrodes of the aforementioned type are:
(1) Fouling—if the electrode surface fouls it is problematic to clean the electrode by applying potential cleaning cycles without destroying the chemical identity of the reference electrode.
(2) In corrosive solution conditions, e.g. a high or low pH, again chemical degradation of the electrode means the reference electrode potential changes with time in the same solution.
(3) AgCl is light sensitive and can photodecompose, again affecting the stability of the electrode.

It is an aim of certain embodiments of the present invention to address one or more of the aforementioned problems. In particular, certain embodiments of the present invention aim to provide an electrochemical sensor comprising both a robust sensing/working electrode and a robust reference electrode. In addition, certain embodiments provide an electrochemical sensor for monitoring low concentrations of a plurality of chemical species in complex chemical environments. Advantageous arrangements combine this functionality in a device which is relatively compact and is suitable for use in the field and/or in remote and/or harsh sensing environments such as for oil and gas applications.

SUMMARY OF INVENTION

The present inventors have realized that while synthetic doped diamond material is the material of choice for use as a sensing electrode in harsh chemical and/or thermal environments, a more robust reference electrode, and optionally a more robust counter electrode, is required if the electrochemical sensor as a whole is to be robust to such conditions. Ideally, it would be desirable to use synthetic doped diamond material for both the sensing (i.e. working) electrode and the reference electrode (and optionally the counter electrode if present). Although diamond is not a true reference electrode (as described in the background section) there are several advantages in using diamond material as a reference electrode including:
(1) It can be easily integrated into a diamond electrode fabrication procedure in an electrochemical sensor which comprises a sensing electrode formed of diamond material.
(2) The diamond material is resistant to chemical and photo-degradation in all solutions, so once in solution, providing the solution composition remains effectively constant the electrode potential will remain constant.
(3) The diamond electrode can be efficiently cleaned using in-situ cleaning cycles so again once in solution, providing the solution composition remains effectively constant the electrode potential will remain constant as the diamond reference electrode can be effectively cleaned to maintain performance.

Despite the aforementioned advantageous features, the proposed use of diamond material has one major problem. That is, a diamond electrode does not fulfil the usual requirement of a reference electrode which is to provide a fixed reference potential with respect to the sensing electrode irrespective of the solution conditions such that voltammetry data can be calibrated and interpreted using the known potential of the reference electrode. The potential of a diamond reference (which is applied with respect to the sensing/working electrode) is unknown for different solutions and thus cannot fulfil this function. Despite this problem, the present inventors consider that the advantages of providing an "all diamond" electrochemical sensor comprising electrodes which are exclusively made of synthetic doped diamond material would be immensely desirable. Furthermore, the present inventors consider that there are a number of ways in which such an electro-chemical sensor may be calibrated in-situ despite the diamond reference electrode not having a fixed reference potential which is de-coupled from solution conditions. Such an in situ calibration is made easier for a diamond electrode material as compared to other types of material because although the potential of a diamond electrode will change from solution to solution, in a given solution a diamond electrode potential will remain relatively constant providing the solution composition remains relatively constant for the previously described reasons. In some configurations a counter electrode may be provided, which is also preferably of diamond, such that the reference, counter and sensing electrode are all diamond. The use of counter electrodes is well known in the art, with the current flow through the sensing electrode being returned to the solution through the counter electrode so that the current flow at the reference electrode is minimised and its voltage stability improved. Given the functionality described above, there are several ways to calibrate the potential of the reference electrode including, for example:

1. In the case of case of anodic stripping voltammetry in which a series of peaks are generated for different species having different stripping potentials, although the potential at which these peaks occur is known with respect to a standard reference electrode, the reference potential for diamond is unknown and will vary from solution to solution. However, it is known that the sequence of species observed in the voltammogram will not change e.g. Cu is easier to oxidise than Pb which is which is easier than Zn etc. . . . Hence by using a spectroscopic technique to independently determine the metal ions present in a solution, the known order of the metal ions can be used to correctly assign a series of peaks in a voltammogram.
2. A known redox couple can be deliberately added to the solution which will not interfere or chemically react with the ions of interest in the solution. This couple will have a known potential versus a standard reference potential but will shift to a new potential when measured against the diamond reference electrode. This shift can then be used to correct for different redox couples in solution measured against the diamond reference electrode.
3. It is possible to produce potential determining ions in-situ, e.g. in-situ CL ion production. To achieve a constant concentration of potential determining ions over the reference electrode one way would be to provide two electrodes in a flow type system where the upstream electrode generates a constant concentration of potential determining ions which flow over the reference electrode. Alternatively, in stationary system one electrode would be positioned over the other. Another possibility would be to provide an additional electrode coated with a metal from which, in use, metal ions can be dissolve off at a constant flux over the reference electrode. Alternatively still, it is possible to change pH conditions to produce a potential determining ion.

In light of the above, according to a first aspect of the present invention there is provided an electrochemical sensor comprising:

a reference electrode formed of an electrically conductive synthetic doped diamond material and configured to be located in electrical contact with a solution to be analysed;

a sensing electrode formed of an electrically conductive synthetic doped diamond material and configured to be located in contact with the solution to be analysed;

an electrical controller configured to apply a voltage to the sensing electrode, to change the applied voltage relative to the reference electrode, and to measure an electric current flowing through the sensing electrode thereby generating voltammetry data; and a calibration system configured to provide an in-situ calibration for assigning peaks in the voltammetry data to chemical species thereby allowing the type and concentration of chemical species in the solution to be determined.

Furthermore, a second aspect of the present invention provides a method of analysing chemical species in a solution using the aforementioned electrochemical sensor, the method comprising:

locating the sensing electrode in contact with a solution to be analysed;

apply a voltage to the sensing electrode;

changing the applied voltage relative to the reference electrode;

measuring an electric current flowing between the reference electrode and the sensing electrode thereby generating voltammetry data;

generating calibration data in-situ within the electrochemical sensor;

calibrating the voltammetry data using the in-situ calibration data;

assigning peaks in the voltammetry data to chemical species;

determining the type and concentration of said chemical species in the solution.

BRIEF DESCRIPTION OF THE DRAWINGS

For a better understanding of the present invention and to show how the same may be carried into effect, embodiments of the present invention will now be described by way of example only with reference to the accompanying drawings, in which:

FIGS. 3a to 3c illustrate the type of data generated using the method shown in FIG. 2;

FIG. 6 is a flow chart illustrating a method of measuring target species using the electrochemical sensor shown in FIG. 5;

FIG. 7 illustrates the type of data generated using the method shown in FIG. 6;

FIG. 8 is a flow chart illustrating a method of measuring target species using in-situ generation of potential determining ions;

DETAILED DESCRIPTION OF CERTAIN EMBODIMENTS

Figure 1:
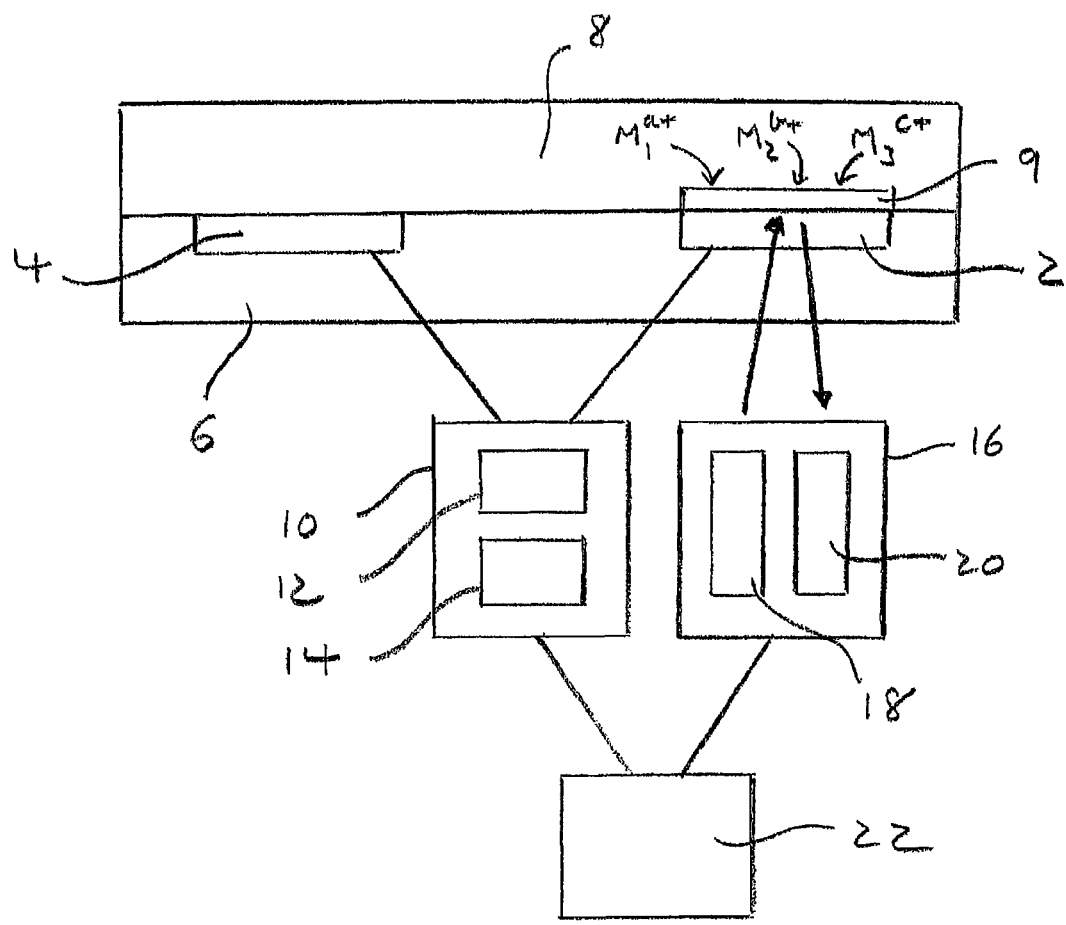
FIG. 1 is a schematic diagram of an electrochemical sensor comprising a diamond reference electrode and an integrated spectrometer for calibrating voltammetric data.

As described in the summary of invention section, if a diamond reference electrode is utilized in an electrochemical sensor then a calibration system is required to provide an in-situ calibration for assigning peaks in voltammetric data to chemical species thereby allowing the type and concentration of chemical species in a solution to be determined. Three examples of suitable calibration systems are described here: (1) an integrated spectrometer; (2) use of a known redox couple; and (3) in-situ generation of potential determining ions.

Integrated Spectrometer

According to one embodiment, the calibration system comprises a spectrometer integrated into the electrochemical sensor and configured to apply a spectroscopic analysis technique to chemical species in the solution or electro-deposited on the sensing electrode and generate spectroscopic data about the identity of the chemical species. The identity of the chemical species determined from the spectroscopic data, in combination with a known peak sequence for the identified chemical species, can be used to assign peaks in the voltammetry data to the identified chemical species thereby allowing the type and concentration of chemical species in the solution to be determined.

For example, in the case of case of anodic stripping voltammetry where a series of peaks are observed, although the potential they occur at with respect to a standard reference electrode is known, the reference potential for diamond is unknown and will vary from solution to solution. However, it is known that the sequence of metals observed in a voltammogram will not change, e.g. Cu is easier to oxidise than Pb which is which is easier than Zn etc. . . . Hence by using a spectroscopic technique to independently determine the metal ions in solution the order of peaks can be correctly assigned.

Such an arrangement therefore allows the possibility to use a non-fixed reference electrode, i.e. a reference electrode which does not provide a fixed reference potential with respect to the sensing electrode irrespective of the solution conditions. Accordingly, a more robust reference electrode can be utilized. In a particularly preferred arrangement a doped diamond material, e.g. boron-doped diamond (BDD) material, can be used for the reference electrode. Diamond electrode material is advantageous for the reasons given in the background section. Furthermore, in such an arrangement a doped diamond material can also be used for the sensing electrode and, if present, a counter electrode (e.g. BDD). As such, an electrochemical sensor can be configured to be self calibrating while also ensuring that only robust materials such as diamond materials are exposed to the solution under testing thus providing a device which is suitable for use in harsh sensing environments.

Various arrangements for integrating the spectrometer into the electrochemical sensor are envisaged. For example, the electrochemical sensor may comprise a window and the spectrometer can be configured to direct the spectroscopic analysis technique through the window towards a front surface of the chemical species electro-deposited onto the sensing electrode. Alternatively, the spectrometer may be configured to direct the spectroscopic analysis technique through the sensing electrode towards a rear surface of the chemical species electro-deposited onto the sensing electrode. Such an arrangement is advantageous in that the spectrometer can be mounted behind the sensing surface such that only a single sensing surface is presented to the solution under testing. In such an arrangement, the material used for the sensing electrode must be transparent to the spectroscopic analysis technique. In this regard, the spectroscopic analysis technique is preferably an elemental analysis technique and, if the species deposited on the sensing electrode are opaque, may be a reflective technique. Examples of suitable techniques include optical techniques based on x-rays or gamma-rays, x-ray fluorescence (XRF) elemental analysis being preferred. Diamond material is advantageous for use with such techniques as it is transparent to such techniques and therefore will not unduly interfere with the spectroscopic analysis.

Embodiments of the present invention thus provide an electrochemical sensor with an integrated spectrometer configured to apply a spectroscopic analysis technique to the electro-deposited chemical species on the sensing electrode in-situ and generate spectroscopic data about the chemical species electro-deposited onto the sensing electrode after deposition and prior to stripping. Such an arrangement has several advantageous features including one or more of the following:
(1) Improved in-situ spectroscopic sensitivity by concentrating species using electro-deposition;
(2) Improved in-situ species discrimination in a multi-species solution by making comparative spectroscopic and electrochemical measurements;
(3) Internal calibration allowing the use of a more robust reference electrode.

Furthermore, the use of diamond as a window material for spectroscopic techniques such as XRF is advantageous since both intrinsic and heavily boron doped diamond are excellent x-ray windows. This contrasts with none x-ray spectroscopic techniques such as UV-visible spectroscopy for which heavily boron doped diamond material is not transparent unless provided as a very thin film as described in prior art arrangements. As such, the use of doped diamond electrodes with x-ray or gamma-ray techniques is advantageous when compared with the use of doped diamond electrode with UV-visible spectroscopy as the material is inherently transparent to such techniques. Furthermore, the use of doped diamond electrodes with x-ray or gamma-ray techniques is advantageous when compared with the use of prior art metallic electrodes which interfere with such techniques. The use of a diamond electrode material is also advantageous as it does not form a mercury amalgam and thus enables mercury detection. A diamond electrode material is also advantageous in that a very high electrode potential can be applied to alter pH via proton or hydroxide generation. For metal ions which are complexed in solution, digests are normally performed to free them so they are available for subsequent reduction. One way to do this is to generate very strong acid (or base) conditions electrochemically. This is also useful for cleaning the electrode. As such, embodiments which utilize diamond electrodes have particular relevance to oil and gas operations when robust remotely operated sensors are needed and environmental monitoring where mercury sensitivity, long term stability, and autonomous calibration is highly advantageous. That said, other x-ray transparent electrodes could be used for certain applications, e.g thin film carbon or graphene on glass, thin film silicon, ITO, or thin film metals (trading x-ray transparency against conductivity).

The minimum configuration of electrodes in this invention is the combination of a reference electrode and a sensing electrode. In some circumstances a counter electrode may be used to avoid passing high currents through the reference electrode. Preferably all these electrodes are diamond. In addition, other diamond electrodes may form part of the system, for example providing secondary or second species sensing electrodes, or to measure or control other properties of the fluid environment, such as temperature, conductivity etc. This provides for a sensor system exposing only diamond to the harsh environment, but providing complex functionality.

The reference and sensing electrodes may be mounted on or over a supporting substrate. In an arrangement in which the spectrometer is configured to perform the spectroscopic analysis through such a substrate then the substrate material should also be selected to be transparent to the spectroscopic technique. Suitable substrates for x-ray techniques include AN, $Al_2O_3$, $SiO_2$, BN, diamond, or other light element materials. Using a low atomic number material for the at least one electrode and substrate enables easy discrimination from target heavy (high atomic number) elements.

Using intrinsic optically transparent diamond as a substrate material and/or as a window material disposed around the at least one electrode at a sensing surface can also enable the use of other optical spectroscopic techniques in addition to, for example, x-ray techniques. Furthermore, although compact x-ray sources are commercially available, it is also envisaged that diamond material may be used as an in-situ x-ray source e.g. heavily boron doped diamond coated with copper. As such, diamond material may be utilized in an electrochemical sensor to combine a number of functional characteristics including one or more of: a boron doped diamond electrode material which is transparent to x-ray spectroscopic techniques; an intrinsic diamond material as a substrate or sensor surface material which is transparent to optical spectroscopic techniques; an in-situ x-ray source for x-ray spectroscopic techniques; a sensing surface which is robust to harsh chemical and thermal environments; and a similarly robust counter and/or reference electrode.

FIG. 1 shows an electrochemical sensor which combines voltammetry and spectroscopic analysis techniques. The electrochemical sensor comprises two electrodes 2, 4 mounted in a support substrate 6. The electrodes 2, 4 are configured to be located in contact with a solution 8 in use. While the illustrated arrangement comprises two electrodes including a sensing electrode 2 and a reference electrode 4, it is to be noted that the supporting substrate may only comprise a sensing electrode 2 with a separate electrode being inserted into the solution to function as a reference electrode 4. In operation, metal species $M_1^{a+}$, $M_2^{b+}$, and $M_3^{c+}$ can be electro-deposited onto the sensing electrode 2 forming a solid metallic layer 9 comprising metal species $M_1$, $M_2$, and $M_3$.

The two electrodes 2, 4 are electrically coupled to an electrical controller 10 which comprises a voltage control unit 12 and a current measurement unit 14. The voltage control unit 12 is configured to apply a potential difference between the two electrodes 2, 4. A counter electrode (not shown) may also be provided if required.

Cyclic voltammetry (CV) refers to a procedure where the sensing electrode 2 is cycled first in one direction to a defined potential and then back again to a defined potential. Typically for stripping voltammetry the potential of the sensing electrode 2, rather than being cycled to a negative potential to reduce cations, is held at a constant potential for a defined time (for low concentrations it may be required to deposit for longer to get a measurable amount on the electrode surface) and then the potential is scanned positive or anodically to produce metal stripping peaks by oxidising all the metal—hence the technique is often referred to as anodic stripping voltammetry (ASV) or different pulse voltammetry (DPV) which means when scanning positively the electrode potential is pulsed to make the current reading more sensitive. Hence a combination of constant potential (deposition) and voltammetric techniques (stripping) are typically used in heavy metal detection using electrochemistry.

During stripping voltammetry the current measurement unit 14 measures current flow around the electrochemical circuit formed by the two electrodes 2, 4, the solution 8, the electrical controller 10 and the electrically couplings therebetween. Alternatively, where a counter electrode is provided, the current measurement unit 14 may measure current flow around the electrochemical circuit formed by the sensing electrodes 2, the counter electrode, the solution 8, the electrical controller 10 and the electrically couplings therebetween. Oxidation (stripping) of metal species results in current flow at certain applied voltages relating to the oxidation potentials of the individual metal species. The magnitude of current flow can be plotted against the changing voltage to generate a stripping voltammogram comprising individual peaks corresponding to oxidation reactions for each of the metallic species. The position and size of each peak can be used to identify the type and quantity of metal species within the solution.

Deposition of species may be via direct or indirect electrochemistry. Direct electrochemistry occurs for a redox couple $A+ne^- \leftrightarrow B$ when A is converted to B through addition of electrons (reduction) whilst B is converted to A via the removal of electrons (oxidation). Typically both A and B are soluble in solution but there are instances where one species is in solid form and the other in solution as is the case for electrodeposition of a metal B from reduction of the associated cationic metal ion A. In contrast, for indirect electrodeposition the product being deposited is not part of a redox couple, as is the case above, but forms due to some precipitation reaction induced electrochemically. Typically this is likely to be an inorganic solid formed from two ions in solution, one which is present naturally, the other which is electrochemically generated. At a defined concentration the solubility product is exceeded causing the solid to precipitate out of solution. For example, if $Ni^{2+}$ ions are present in solution and $OH^-$ ions are generated electrochemically by the reduction of water this leads to the precipitation of nickel hydroxide on the electrode surface [see, for example, L. A. Hutton et al. "Electrodeposition of Nickel Hydroxide Nanoparticles on Boron-Doped Diamond Electrodes for Oxidative Electrocatalysis", J. Phy. Chem. 2010]. Decreasing the pH, e.g. by oxidising water to produce protons, may also be used to promote a reaction resulting in the formation of a solid species in solution. Additionally many inorganic solids have a pH dependant solubility for example under acidic conditions calcium carbonate is soluble however as the pH is increased the solubility will decrease causing calcium carbonate to precipitate out of solution. Hence precipitation reactions can be induced simply by changing pH electrochemically.

The illustrated electrochemical sensor differs from a standard stripping voltammeter in that the reference electrode 4 is made of diamond material and the sensor comprises an integrated spectrometer 16 configured to perform elemental analysis of solid species 9 which have been electro-deposited onto the sensing electrode 2. The spectrometer comprises an emitter 18 and a detector 20. In the illustrated arrangement, the spectrometer is configured to perform a spectroscopic analysis of the solid species 9 through the sensing electrode 2 and support substrate 6. As such, the electrode 2 and support substrate 6 should be made of a material which is transparent to the spectroscopic analysis. For example, the spectroscopic analysis may utilize an x-ray technique such as x-ray fluorescence (XRF) elemental analysis and the electrode 2 and substrate 6 may be made of a low atomic number material such as diamond. The electrode 2 may be formed of a boron doped diamond material such that it is electrically conductive while the support substrate 6 may be formed of an intrinsic diamond material. Both these materials are transparent to x-ray analysis.

The intrinsic diamond material also has good transmittance for wavelengths from the infrared to the ultraviolet and thus further spectroscopic analysis of the solution 8 may be performed using these wavelengths through regions of the substrate 6 between the electrodes 2, 4.

The electrochemical sensor further comprises a data processor 22 which is configured to receive data from both the electrical controller 10 and the spectrometer 16. This data will be in the form of stripping voltammetry data from the electrical controller 10 and spectroscopic data from the spectrometer 16. Both types of data are capable of given information about the type and quantity of metal species electro-deposited onto the sensing electrode 2. However, in the case that two or more peaks in the stripping voltammetry data overlap for different species, the spectroscopic data can be utilized to determine the number and type of different species present to aid in interpretation of the stripping voltammetry data and function as a tool to deconvolute the data and correctly characterize the components within the solution. Alternatively, for certain applications the electrical controller may function only as a means of depositing chemical species from solution for spectroscopic analysis. In this case, qualitative spectroscopy can identify the type of species present whereas quantitative spectroscopy can determine both the type and quantity of species. Use of a diamond material for the electrode 2 is advantageous in this regard as a large potential can be applied to electro-deposit a large range of target species for spectroscopic analysis.

It is to be noted that while the electrochemical sensor illustrated in FIG. 1 is configured such that the reference electrode is in physical contact with the solution to be analysed, it is also possible to place the reference electrode into a separate solution, the solution conditions of which can be controlled. In this case the solution in which the reference electrode is placed can be electrically connected to the solution in which the sensing electrode is placed via a salt bridge. Accordingly, while in most cases the reference electrode will be placed in physical contact with the solution to be analysed, a minimum requirement is that the reference electrode is in electrical contact with the solution to be analysed.

Figure 2:
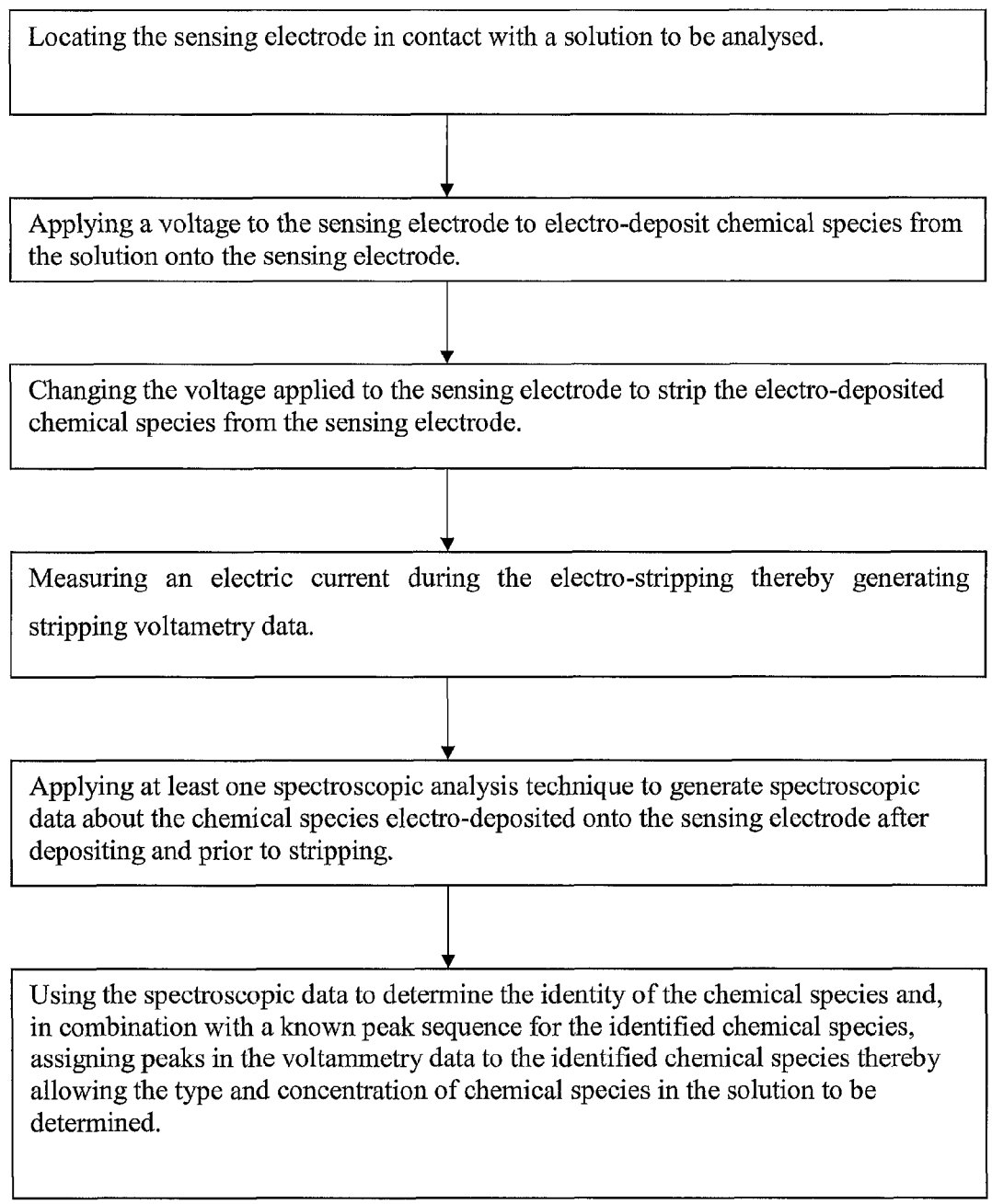
FIG. 2 is a flow chart illustrating a method of measuring target species using the electrochemical sensor shown in FIG. 1.

FIG. 2 is a flow chart illustrating a method of measuring target species using the electrochemical sensor shown in FIG. 1. The method comprises:

locating the sensing electrode in contact with a solution to be analysed (26);
applying a voltage to said sensing electrode to electro-deposit chemical species from the solution onto the sensing electrode (28);
changing the voltage applied to the sensing electrode to strip the electro-deposited chemical species from the sensing electrode (30);
measuring an electric current during the electro-stripping thereby generating stripping voltametry data (32);
applying at least one spectroscopic analysis technique to generate spectroscopic data about the chemical species electro-deposited onto the at least one electrode after depositing and prior to stripping (34);
using the spectroscopic data to determine the identity of the chemical species and, in combination with a known peak sequence for the identified chemical species, assigning peaks in the voltammetry data to the identified chemical species thereby allowing the type and concentration of chemical species in the solution to be determined (36).

The spectroscopic analysis may be applied during the same deposition and stripping cycle as the voltammetric data is obtain. Alternatively, the spectroscopic analysis may be performed in a separate deposition and stripping cycle to that in which the voltammetric data is obtain. For example, a deposition and stripping cycle may be performed during which current measurements are taken to generate voltammetric data. Subsequently, a further deposition and stripping cycle may be performed during which spectroscopic data is obtained. The spectroscopic analysis may alternatively be performed during a first deposition and stripping cycle and then the spectroscopic data used for analysing one or a sequence of subsequent deposition and stripping cycles during which voltammetric data is obtained. This may be advantageous where a longer deposition time is required to increase the concentration of species on the sensing electrode to a sufficient level to obtain good spectroscopic data regarding the type of chemical species present in solution. Subsequently, a series of shorter deposition and stripping cycles can be performed to track the concentration of species using voltammetric data with the spectroscopic data from the first cycle being used to assign peaks in a series of voltammograms.

FIGS. 3a to 3c illustrate an example of data generated using the method shown in FIG. 2. FIG. 3a shows a stripping voltammogram generated by the electrical controller. The stripping voltammogram comprises oxidation peaks for three species $M_1$, $M_2$, and $M_3$. Although there is some overlap between the peaks, they are sufficiently separated that the stripping voltammogram can be deconvoluted into three separate voltammograms, one for each species as illustrated in FIG. 3b. These voltammograms can be used to identify the type and quantity of each species by peak location and area measurements. In practice, this can be done numerically or by generating pictorial representations of the voltammetry data. For example, the composite voltammogram can be deconvoluted using Fourier analysis techniques. However, unlike standard voltammetry peak locations cannot be compared to a reference potential to identify different target species of interest if a non-fixed reference electrode utilized. Accordingly, spectroscopic data may be utilized as discussed below.

FIG. 3c illustrates an XRF spectrum obtained by the spectrometer 16. The spectrum $K_\alpha$, $K_\beta$, and second order $K_\alpha''$ lines for the three metal species previously discussed. This spectroscopic information can be used to determine the type of species electro-deposited on the sensing electrode 2. In the illustrated XRF spectrum species $M_1$, $M_2$, and $M_3$ can be identified. Furthermore, if it is known that the species $M_1$ oxidizes at the lowest potential and that species $M_3$ oxidizes at the highest potential such that the sequence of peaks in a voltammogram is $M_1$, $M_2$, $M_3$, then the identified metal can be assigned to the individual peaks in the voltammogram. The voltammetry data can then be used to determine the quantity of species. As voltammetry data is more sensitive than spectroscopic measurements, particularly at low concentrations, the voltammetry data will give more accurate concentration data even if the spectroscopic data may also be used in a quantitative manner to determine concentrations.

Figure 4:
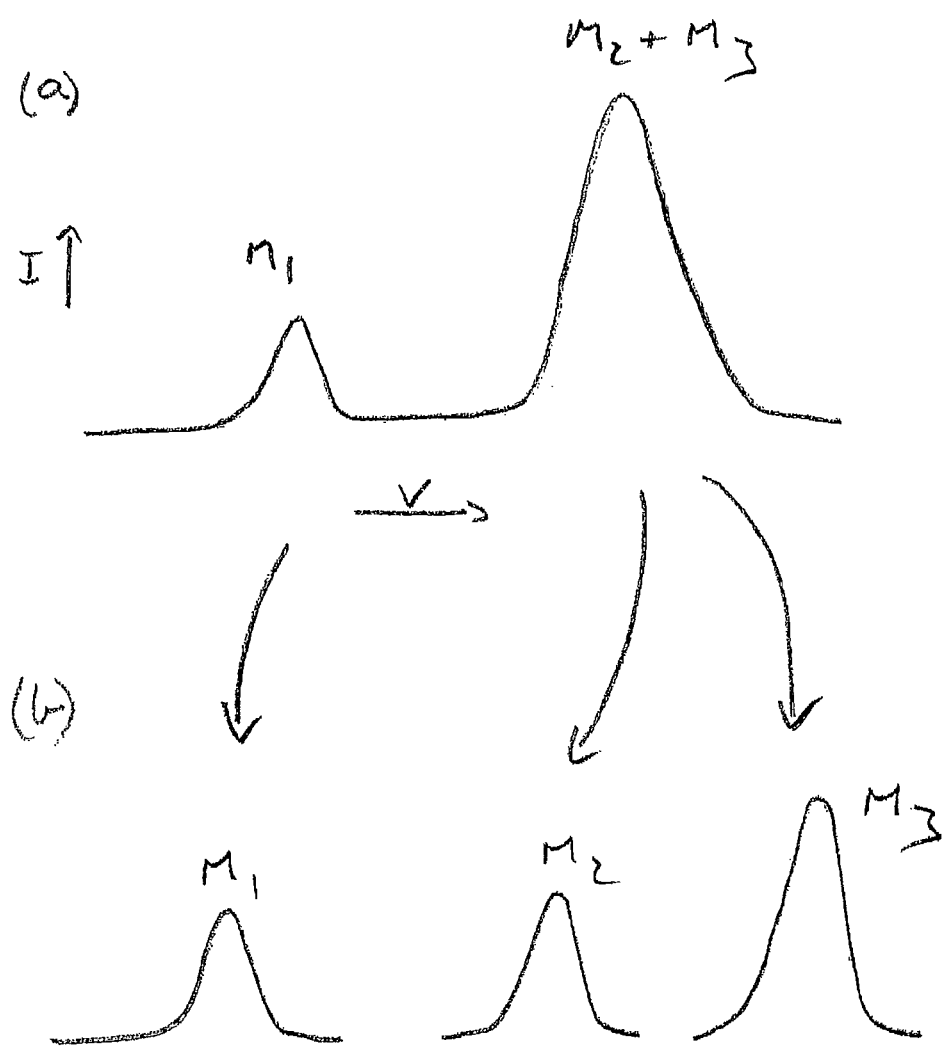
FIGS. 4a to 4c illustrate another example of the type of data generated using the method shown in FIG. 2.

Furthermore, in the case that one or more of the target species have overlapping peak in the stripping voltammetry data such that the data cannot be readily be deconvoluted, the spectroscopic data can either be used as a means to deconvolute the voltammetry data or otherwise used instead of the voltammetry data to identify and quantify individual target species. For example, FIG. 4a shows a stripping voltammogram for three target species $M_1$, $M_2$, and $M_3$ where the peaks for species $M_2$ and $M_3$ completely overlap. Decovolution of this voltamogram without any other information may result in the erroneous identification of only two species, e.g. $M_1$ and $M_2$ only or $M_1$ and $M_3$ only, or otherwise give an ambiguous result indicating that $M_2$ and/or $M_3$ may be present. In this case, spectroscopic data as indicated in FIG. 3c can be used to correctly deconvolute the composite voltammogram illustrated in FIG. 4a into its three constituent parts as shown in FIG. 4(b). Alternatively, the spectroscopic data could be used on its own, the electrical controller merely being utilized as a means of depositing species for spectroscopic analysis. However, in practice the voltammetry data and the spectroscopic data can provide complimentary information. For example, the spectroscopic data can give elemental information which may not be resolved in the voltammetry data whereas the voltammetry data may give information relating to the oxidative state of species within the solution which cannot be identified from the spectroscopic data. The voltammetry data will also be more sensitive to species present at low concentration.

As previously discussed, the use of a diamond electrode material in combination with an x-ray spectroscopic analysis technique is considered to be particularly preferable for implementing the present invention. Compact x-ray sources are commercially available. Alternatively, the diamond material may be used as an in-situ x-ray source, e.g. by coating a boron doped diamond material with a metal such as copper to form an x-ray source.

The integration of a spectrometer into an electrochemical sensor in the manner described herein will increase functionality and performance in terms of resolution and sensitivity for analysing solutions which contain a plurality of different target species of interest. Previously, for solutions which comprise a number of different species having overlapping voltammetry peaks, for example a number of heavy metal species having similar electrochemical potentials, it may only have been possible to determine the total species content, e.g. the total heavy metal content. In contrast, embodiments of the present invention allow identification and quantification of a large range of different species in a single solution even when voltammetry peaks overlap.

Various different electrode structures may be utilized with the combined electrochemical/spectroscopic techniques described herein. Some examples of prior art diamond electrode arrangements are discussed in the background section. In addition to the provision of a diamond sensing electrode, in accordance with embodiments of the present invention it is also advantageous to provide a diamond reference electrode. If the reference electrode is made of, for example, Ag/AgCl or $Hg/Hg_2Cl_2$ (common reference electrodes) then the reference electrode may be contaminated or attacked in aggressive environments. Using a diamond reference is preferable as it will not be etched and has a high dimensional stability in aggressive chemical/physical environments. Providing an integrated spectrometer to aid in assigning voltammetry allows such a non-fixed potential reference electrode to be utilized.

Other useful techniques may be combined with the electrochemical/spectroscopic techniques described herein. For example, differential potential pulse programmes can be used to increase sensitivity. Furthermore, the temperature of the sensing electrode can be changed to alter mass transport, reaction kinetics, and alloy formation. For example, heating during stripping voltammetry can aid in increasing peak signals. Heating during deposition can aid formation of better alloys and can also increase mass transport shortening deposition times and/or increasing deposition to within the detection sensitivity of spectroscopic techniques such as XRF. Accordingly, in certain arrangements configured to detect very low concentrations of chemical species in solution a heater may be provided within the electrochemical sensor for heating the sensing electrode to increase deposition to within the limits of the spectroscopic analysis technique over a defined time period. The use of diamond material for the sensing electrode is also useful in this regard as diamond material can be heated and cooled very quickly. The high electrode potential of diamond material can also be utilized to alter pH via electrochemical generation. For metal ions which are complexed in solution, digests are normally performed to free them so they are available for subsequent reduction. One way to do this is to generate very strong acid (or base) conditions electrochemically. This is also useful for cleaning the electrode. Other cleaning techniques may involve abrasive cleaning and/or heating.

Use of a Known Redox Couple

As an alternative to the use of an integrated spectrometer as described above, the calibration system may be configured to use a known redox couple in the solution of interest in order to calibrate voltammetry data.

Figure 5:
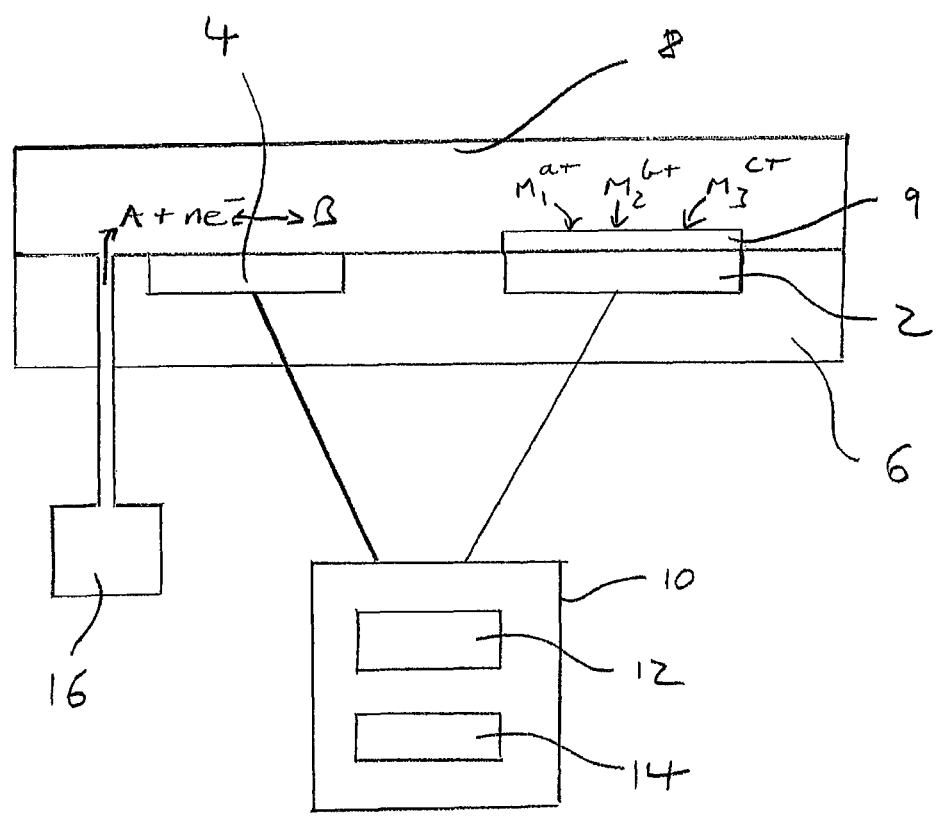
FIG. 5 is a schematic diagram of an electrochemical sensor comprising a diamond reference electrode and configured to use a known redox couple for calibrating voltammetric data.

FIG. 5 shows an electrochemical sensor for use in such a technique. The electrochemical sensor comprises two electrodes 2, 4 mounted in a support substrate 6. The electrodes 2, 4 are configured to be located in contact with a solution 8 in use. While the illustrated arrangement comprises two electrodes including a sensing electrode 2 and a reference electrode 4, it is to be noted that the supporting substrate may only comprise a sensing electrode 2 with a separate electrode being inserted into the solution to function as a reference electrode 4. In operation, metal species $M_1^{a+}$, $M_2^{b+}$, and $M_3^{c+}$ can be electro-deposited onto the sensing electrode 2 forming a solid metallic layer 9 comprising metal species $M_1$, $M_2$, and $M_3$.

The two electrodes 2, 4 are electrically coupled to an electrical controller 10 which comprises a voltage control unit 12 and a current measurement unit 14. The voltage control unit 12 is configured to apply a potential difference between the two electrodes 2, 4. A counter electrode (not shown) may also be provided if required and is preferably also made of a doped diamond material such as BDD in contrast to known counter electrodes such as high surface area platinum gauzes.

In this arrangement a spectrometer is not required. Rather the voltammetric signal from a known redox couple in the solution is used to calibrate the voltammetric data. The redox couple may be one which is already known to be present in the solution to be analysed. However, in order to ensure that a clear reference signal is provided it can be advantageous to configure a calibration system to introduce a predetermined quantity of the known redox couple into the solution to be analysed. In the illustrated embodiment an injection system 16 is provided for injecting a redox couple species A into the solution to be analyzed.

The redox couple is represented by the equation $A+ne^- \leftrightarrow B$ when A is converted to B through addition of electrons (reduction) whilst B is converted to A via the removal of electrons (oxidation). Both A and B may be soluble in solution. Alternatively one species may be in solid form and the other in solution as is the case for electrodeposition of a metal B from reduction of the associated cationic metal ion A.

The electrical controller can be used to generate voltammetric data by applying voltages to the electrodes and measuring the associated current. The voltammetric data will include a signal from the redox couple. The data can then be calibrated as shown in the flow chart of FIG. 6:

- identify the peak in the voltammetry data associated with a known redox couple in the solution, the known redox couple having a known potential versus a standard reference potential (60);
- measure a shift in the peak of the known redox couple relative to its known potential versus the standard reference potential (62);
- use the measured shift to calibrate the voltammetry data relative to the standard reference potential (64); and
- use the calibrated voltammetry data to assign peaks to chemical species which have a known potential relative to the standard reference potential (66).

Although the redox couple will have a known potential versus a standard reference potential, the potential will shift when using a non-standard reference such a diamond reference electrode. If numerous peaks are present in a complex voltammogram, the redox couple should be selected such that it can still be readily identified despite this shift. As such, the redox couple may be selected to have a peak position sufficiently far removed from the other peaks that it can still be uniquely identified. Alternatively, the redox couple may be provided at a concentration significantly different to that expected for target species of interest such that the peak height will be significantly different to the target species and can thus be uniquely identified. Advantageously, the known redox couple is selected to be one which does not interfere or chemically react with ions of interest in the solution.

To illustrate, FIG. 7(a) shows a voltammogram comprising 4 peaks. It is known that one of the peaks relates to an added redox couple for calibration and that the potential of the added redox couple relative to a standard reference potential is Vs. The added redox couple species is selected to have a potential removed from the expected potentials of target species in the solution and to have a greater concentration than expected for the species of interest in the solution being analysed. As such, it can be identified that the peak associated with the added redox couple is the right-most peak in the voltammogram. The shift S in the peak position relative Vs can then be measured and corrected for across the voltammogram such that all the peaks are shifted to the right by an amount S. Once the redox couple peak has been identified, the shift in potential can be measured. The other peaks in the voltammogram associated with target species of interest will also have shifted in a similar manner. Once the shift has been quantified it can be corrected for in order to produce voltammetric data which is calibrated relative to a standard potential as shown in FIG. 7(b). The peaks of the calibrated data shown in FIG. 7(b) can then be assigned based on known potentials versus the standard reference potential to which the data has been calibrated.

The redox couple illustrated in FIGS. 7a and 7b is one in which species B is a solid, e.g. a metal which undergoes deposition and stripping. As an alternative, both species A and species B may be soluble. In that case, a separate voltammetry calibration may be performed in-situ, e.g. prior to or after performing stripping voltammetry. For example, cyclic voltammetry may be used to measure an added redox couple, evaluate a shift in its peak position relative to its known potential relative to a standard reference potential, and then use this shift to calibrate the stripping voltammetry data.

In-Situ Generation of Potential Determining Ions

Yet another alternative for calibrating an electrochemical sensor comprising a diamond reference electrode is to produce a chemical environment around the diamond reference electrode in which the diamond electrode has a known potential. Such a method requires the in-situ generation of ions over the diamond reference electrode to tune the diamond reference electrode towards the known potential as shown in the flow chart of FIG. 8:

produce a constant and known concentration of potential determining ions in-situ over the reference electrode, the reference electrode having a known potential in a solution comprising said concentration of potential determining ions (80);

use the known potential to calibrate the voltammetry data (82); and use the calibrated voltammetry data to assign peaks to chemical species based on their known potential (84).

Figure 9:
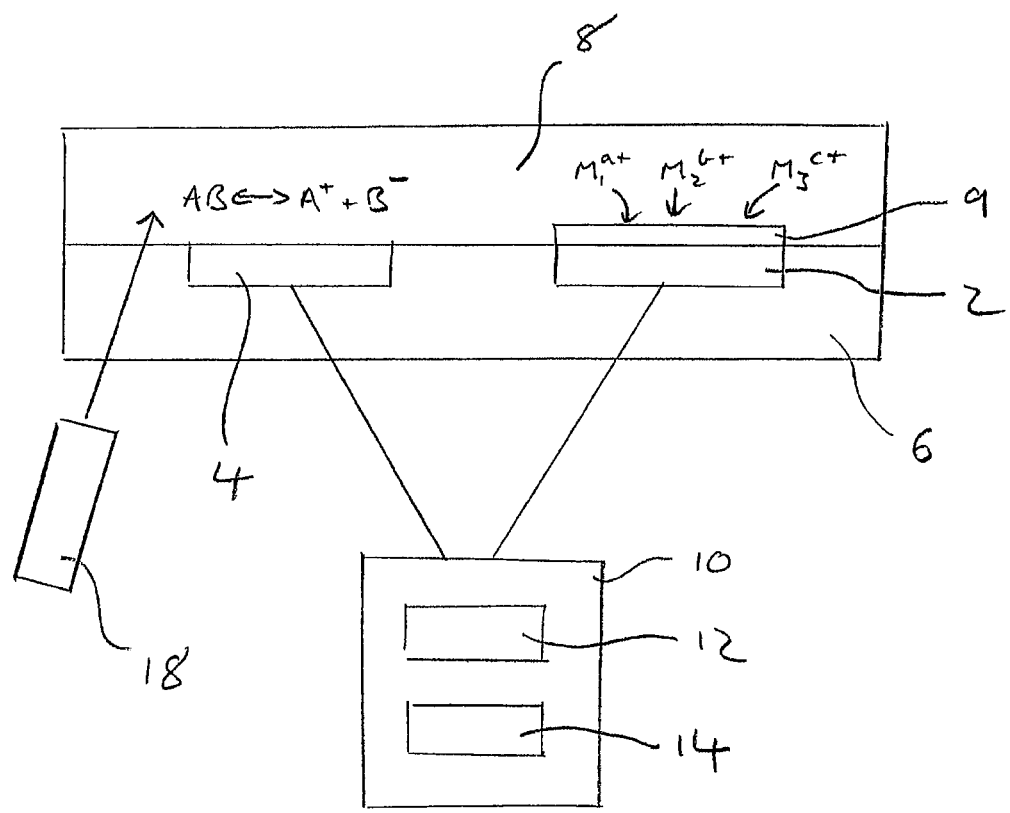
FIG. 9 is a schematic diagram of an electrochemical sensor comprising a diamond reference electrode and a light source configured to produce potential determining ions over the reference electrode by photodecomposition for calibrating voltammetric data.

Various possible ways are envisaged for implementing this technique. For example, the calibration system may comprise a light source configured to produce the potential determining ions by, for example, photodecomposition to tune the reference electrode to the known potential. FIG. 9 shows an electrochemical sensor for use in such a technique. The electrochemical sensor comprises two electrodes 2, 4 mounted in a support substrate 6. The electrodes 2, 4 are configured to be located in contact with a solution 8 in use. While the illustrated arrangement comprises two electrodes including a sensing electrode 2 and a reference electrode 4, it is to be noted that the supporting substrate may only comprise a sensing electrode 2 with a separate electrode being inserted into the solution to function as a reference electrode 4. In operation, metal species $M_1^{a+}$, $M_2^{b+}$, and $M_3^{c+}$ can be electrodeposited onto the sensing electrode 2 forming a solid metallic layer 9 comprising metal species $M_1$, $M_2$, and $M_3$.

The two electrodes 2, 4 are electrically coupled to an electrical controller 10 which comprises a voltage control unit 12 and a current measurement unit 14. The voltage control unit 12 is configured to apply a potential difference between the two electrodes 2, 4. A counter electrode (not shown) may also be provided if required.

A light source 18 is integrated into the electrochemical sensor and configured to produce potential determining ions above the reference electrode by photodecomposition to tune the reference electrode towards a known potential. The photodecomposition reaction is illustrated by the equation $AB \leftrightarrow A^+ + B^-$. The light source in controlled to produce a constant and known concentration of potential determining ions $A^+$, $B^-$ in-situ over the reference electrode and the reference electrode has a known potential in a solution comprising said concentration of potential determining ions. As such, the light source can be used to tune the diamond reference electrode towards the known potential. This known potential can then be used to calibrate the voltammetry data and assign peaks to chemical species based on their known potential.

Figure 10:
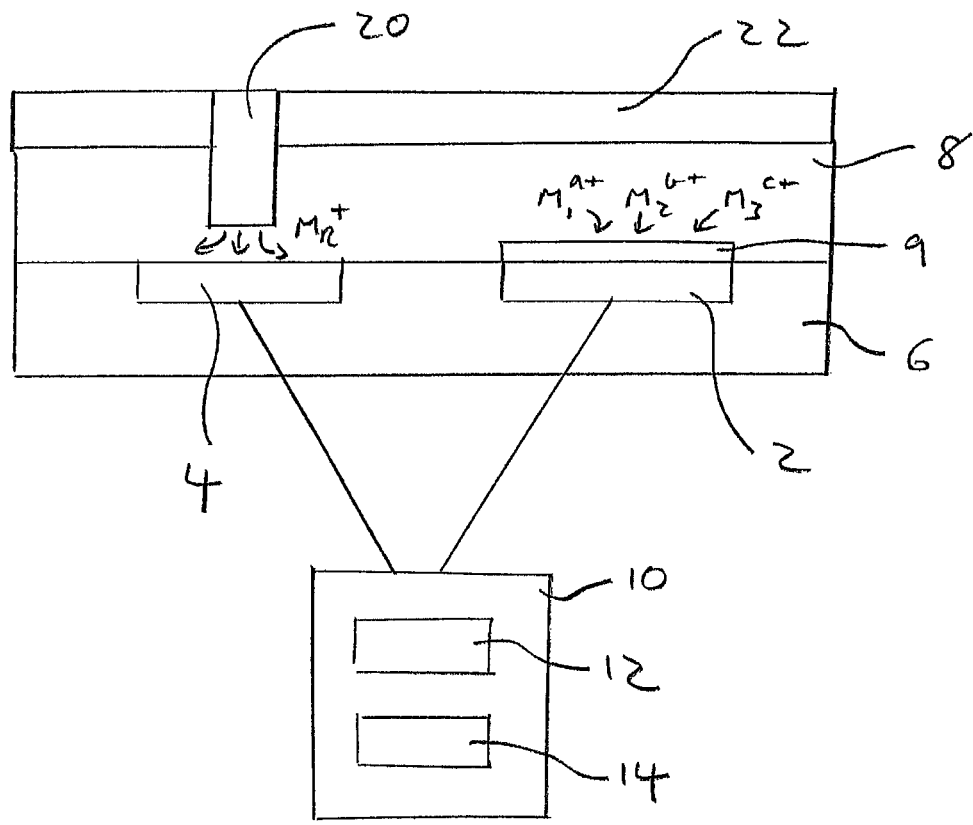
FIG. 10 is a schematic diagram of an electrochemical sensor comprising a diamond reference electrode and a calibration electrode configured to form potential determining ions over the reference electrode for calibrating voltammetric data.

FIG. 10 shows an alternative arrangement in which the light source is replaced with a calibration electrode 20 configured to form potential determining ions over the reference electrode for calibrating voltammetric data. Otherwise the electrochemical sensor is similar in structure to that previously described and like numerals have been given to like parts. In the illustrated embodiment, the calibration electrode comprises a metal, e.g. Pb, and the potential determining ions are metal ions formed by dissolution of the metal. In such an arrangement, the metal electrode may become depleted over time and require replacement. As such, a mounting arrangement 22 may be provided and configured such that the calibration electrode can readily be removed and replaced when required. Alternatively, the calibration electrode may be configured to change pH conditions in the solution by generating protons or hydroxide ions as potential determining ions or to promote a reaction over the reference electrode to tune the reference electrode towards said known potential. In this case, the calibration electrode may be made of a robust material such as synthetic doped diamond material.

For the aforementioned arrangements, it may also be desirable to segregate the potential determining ions from the sensing electrode to prevent interference at the sensing electrode. In this regard, the solution over the reference electrode may be separated from the main solution under test using, for example, a frit.

Figure 11:
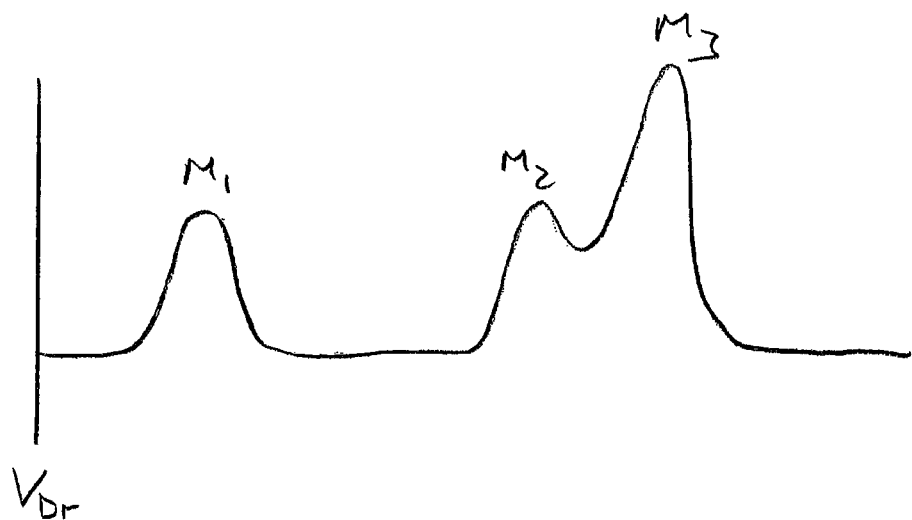
FIG. 11 illustrates the type of data generated using the method and apparatus shown in FIGS. 8 to 10.

FIG. 11 illustrates the type of data generated using the method and apparatus shown in FIGS. 8 to 10. Voltammetric data is generated using a diamond electrode which has been tuned towards a known potential $V_{Dr}$ by manipulating and controlling the solution environment around the diamond electrode. As such, the peaks in the data can be assigned by measuring the potentials relative to the known potential of the diamond reference electrode.

In addition to the three examples described above, a fourth possibility for assigning voltammetric data in the absence of a standard reference electrode is described below.

Peak Tracking Over Time

It may be possible in certain circumstance to use the fingerprint of one or more voltammetry peaks in order to assign individual peaks without requiring a fixed reference potential. Prior knowledge of the expected species types and solution conditions may aid this process.

This prior knowledge of the expected species and solution conditions may come from a previous measurement. Thus, separately, or in combination with any of the above techniques, a further technique for peak identification is peak tracking. By making repeat measurements at a sufficient frequency it is possible to follow individual peaks in the solution, and so retain their identity even as conditions or concentrations change. The sampling rate needs to be selected appropriately to meet the rates of change expected, and provided at any one time identification of one peak is retained, then it may be possible to temporarily lose and regain the identification of another peak by using the first peak as a reference.

In the case of using in-situ generation of potential determining ions and/or when using a known redox couple as described previously, this approach provides two further possibilities: (1) deliberate time variation of the species concentration (e.g. of the potential determining ions or the known redox couple species) can be used to assist in peak identification; and (2) the necessity to hold the concentration (e.g. of the potential determining ions or the known redox couple species) at a fixed value is removed provided that at at least one concentration during the time varying profile it is possible to measure the concentration sufficiently to use data from this point to provide the expected location of the peak. This makes in-situ species generation much simpler and more flexible in application.

SUMMARY

Any of the methods previously described may be utilized alone, or in combination, to provide in-situ calibration for an electrochemical sensor which comprises a diamond reference electrode in addition to a diamond sensing electrode. Other possibilities may also be envisaged.

In addition, the calibration system may comprise a cleaning system configured to perform in-situ cleaning of the reference electrode. For example, a cleaning system may be configured to clean the reference electrode using one or more of: abrasive cleaning which physical removes chemical species adhered to the reference electrode surface; heating of the reference electrode to break down adhesion of chemical species on the reference electrode surface; chemical cleaning by electro-chemical generation of protons or hydroxide ions in situ. In this regard, diamond is a particularly useful material for the reference electrode as it is robust to harsh cleaning techniques and can thus be cleaned to generate a good reference surface without undue damage.

Embodiments of the present invention have been described in relation to stripping voltammetry techniques. In such arrangements, the electrical controller is configured to apply a voltage to the sensing electrode to electro-deposit chemical species from the solution onto the sensing electrode, to change the applied voltage to strip the electro-deposited chemical species from the sensing electrode, and to measure an electric current flowing through the sensing electrode during stripping to generate stripping voltammetry data. However, it is envisaged that other voltammetric techniques may be utilized with the present invention such as cyclic voltammetry.

While the electrodes may conceivably be configured in various ways, it is envisaged that in one advantageous arrangement the reference electrode and the sensing electrode are integrated into a single sensing component formed of synthetic diamond material. In such an arrangement the sensing component may comprise a sensing surface formed by the reference electrode, the sensing electrode and intrinsic non-conductive diamond material disposed therebetween. As such, the sensor may be configured to present only, or substantially only, diamond components to the fluid under testing. Such an arrangement is highly advantageous for use in harsh environments.

While this invention has been particularly shown and described with reference to preferred embodiments, it will be understood to those skilled in the art that various changes in form and detail may be made without departing from the scope of the invention as defined by the appendant claims.

The invention claimed is:

1. An electrochemical sensor comprising:
 a reference electrode formed of an electrically conductive synthetic doped diamond material and configured to be located in electrical contact with a solution to be analysed;
 a sensing electrode formed of an electrically conductive synthetic doped diamond material and configured to be located in contact with the solution to be analysed;
 an electrical controller configured to apply a voltage to the sensing electrode, to change the applied voltage relative to the reference electrode, and to measure an electric current flowing through the sensing electrode thereby generating voltammetry data; and
 a calibration system configured to provide an in-situ calibration for assigning peaks in the voltammetry data to chemical species thereby allowing the type and concentration of chemical species in the solution to be determined.

2. An electrochemical sensor according to claim 1, wherein the calibration system comprises a spectrometer integrated into the electrochemical sensor and configured to apply a spectroscopic analysis technique to chemical species in the solution or electro-deposited on the sensing electrode and generate spectroscopic data about the identity of the chemical species, whereby the identity of the chemical species determined from the spectroscopic data, in combination with a known peak sequence for the identified chemical species, can be used to assign peaks in the voltammetry data to the identified chemical species thereby allowing the type and concentration of chemical species in the solution to be determined.

3. An electrochemical sensor according to claim 2, wherein the calibration system comprises a window and the spectrometer is configured to direct the spectroscopic analysis technique through the window towards a front surface of the chemical species electro-deposited onto the sensing electrode.

4. An electrochemical sensor according to claim 2, wherein the spectrometer is configured to direct the spectroscopic analysis technique through the sensing electrode towards a rear surface of the chemical species electro-deposited onto the sensing electrode.

5. An electrochemical sensor according to claim 2, wherein the spectrometer is configured to perform an elemental analysis technique.

6. An electrochemical sensor according to claim 2, wherein the spectrometer is configured to perform a reflective technique.

7. An electrochemical sensor according to claim 2, wherein the spectrometer is configured to perform a spectroscopic analysis technique comprising x-rays or gamma-rays.

8. An electrochemical sensor according to claim 2, wherein the spectrometer is configured to perform a spectroscopic analysis technique comprising x-ray fluorescence elemental analysis.

9. An electrochemical sensor according to claim 1, wherein the calibration system is configured to:
 identify a peak in the voltammetry data associated with a known redox couple in the solution, the known redox couple having a known potential versus a standard reference potential;
 measure a shift in the peak of the known redox couple relative to its known potential versus the standard reference potential;
 use the measured shift to calibrate the voltammetry data relative to the standard reference potential; and
 use the calibrated voltammetry data to assign peaks to chemical species which have a known potential relative to the standard reference potential.

10. An electrochemical sensor according to claim 9, wherein the calibration system is configured to introduce a predetermined quantity of the known redox couple into the solution.

11. An electrochemical sensor according to claim 9, wherein the known redox couple is one which does not interfere or chemically react with ions of interest in the solution.

12. An electrochemical sensor according to claim 1, wherein the calibration system is configured to:
produce an approximately constant and known concentration of potential determining ions in-situ over the reference electrode, the reference electrode having a known potential in a solution comprising said concentration of potential determining ions;
use the known potential to calibrate the voltammetry data; and
use the calibrated voltammetry data to assign peaks to chemical species based on their known potential.

13. An electrochemical sensor according to claim 12, wherein the calibration system comprises a light source configured to produce the potential determining ions by photodecomposition to tune the reference electrode towards said known potential.

14. An electrochemical sensor according to claim 12, wherein the calibration system comprises a calibration electrode configured to form the potential determining ions over the reference electrode in use to tune the reference electrode towards said known potential.

15. An electrochemical sensor according to claim 14, wherein the calibration electrode comprises a metal and the potential determining ions are metal ions formed by dissolution of the metal.

16. An electrochemical sensor according to claim 14, wherein the calibration electrode is configured to change pH conditions in the solution by generating protons or hydroxide ions to promote a reaction over the reference electrode to tune the reference electrode towards said known potential.

17. An electrochemical sensor according to claim 12, wherein the calibration system is configured to segregate the potential determining ions from the sensing electrode.

* * * * *